United States Patent
Pellico

(10) Patent No.: US 7,060,256 B2
(45) Date of Patent: *Jun. 13, 2006

(54) INCREASED PEROXIDE CONTENT TOOTH BLEACHING GEL

(75) Inventor: Michael A. Pellico, Los Angeles, CA (US)

(73) Assignee: Discus Dental, Inc., Culver City, CA (US)

(*) Notice: Subject to any disclaimer, the term of this patent is extended or adjusted under 35 U.S.C. 154(b) by 12 days.

This patent is subject to a terminal disclaimer.

(21) Appl. No.: 10/758,915

(22) Filed: Jan. 16, 2004

(65) Prior Publication Data

US 2004/0146467 A1 Jul. 29, 2004

Related U.S. Application Data

(63) Continuation of application No. 10/349,725, filed on Jan. 22, 2003, now abandoned, which is a continuation of application No. 09/659,483, filed on Sep. 11, 2000, now abandoned.

(60) Provisional application No. 60/153,162, filed on Sep. 9, 1999.

(51) Int. Cl.
- A61K 8/20 (2006.01)
- A61K 8/22 (2006.01)
- A61K 8/30 (2006.01)
- A61K 8/38 (2006.01)
- A61B 19/02 (2006.01)

(52) U.S. Cl. ............... 424/53; 424/401; 433/215; 433/216; 206/63.5; 206/571

(58) Field of Classification Search ............ 424/53, 424/401; 433/215, 216
See application file for complete search history.

(56) References Cited

U.S. PATENT DOCUMENTS

| | | | |
|---|---|---|---|
| 4,528,180 A | 7/1985 | Schaeffer | |
| 4,687,663 A | 8/1987 | Schaeffer | |
| 4,849,213 A | 7/1989 | Schaeffer | |
| 4,990,089 A | 2/1991 | Munro | |
| 5,486,350 A * | 1/1996 | Norfleet et al. | 424/49 |
| 5,648,064 A | 7/1997 | Gaffar et al. | |
| 5,713,738 A | 2/1998 | Yarborough | |
| 5,718,886 A | 2/1998 | Pellico | |
| 5,725,843 A * | 3/1998 | Fischer | 424/49 |
| 5,785,527 A | 7/1998 | Jensen et al. | |
| 5,855,870 A | 1/1999 | Fischer | |
| 5,858,332 A | 1/1999 | Jensen et al. | |
| 5,902,568 A | 5/1999 | Ryles et al. | |
| 5,922,307 A | 7/1999 | Montgomery | |
| 5,928,628 A | 7/1999 | Pellico | |
| 6,036,943 A | 3/2000 | Fischer | |
| 6,106,812 A | 8/2000 | Prencipe et al. | |
| 6,110,446 A | 8/2000 | Principe et al. | |
| 6,116,900 A | 9/2000 | Ostler | |
| 6,162,055 A | 12/2000 | Montgomery et al. | |
| 6,280,708 B1 | 8/2001 | Ryles et al. | |
| 6,306,370 B1 | 10/2001 | Jensen et al. | |
| 6,309,625 B1 | 10/2001 | Jensen et al. | |
| 6,312,666 B1 | 11/2001 | Oxman et al. | |
| 6,312,671 B1 | 11/2001 | Jensen et al. | |
| 6,322,774 B1 | 11/2001 | Jensen et al. | |
| 6,343,933 B1 | 2/2002 | Montgomery et al. | |
| 6,365,134 B1 | 4/2002 | Orlowski et al. | |
| 6,368,576 B1 | 4/2002 | Jensen et al. | |
| 6,503,485 B1 | 1/2003 | Allred | |
| 6,555,020 B1 * | 4/2003 | Chadwick et al. | 252/186.26 |

FOREIGN PATENT DOCUMENTS

| | | |
|---|---|---|
| WO | WO 98/10737 | 3/1998 |
| WO | WO 98/30494 | 7/1998 |
| WO | WO 99/62472 | 12/1999 |
| WO | WO 00/16737 | 3/2000 |
| WO | WO 00/28953 | 5/2000 |
| WO | WO 01/17481 | 3/2001 |

OTHER PUBLICATIONS

Discus Dental Web Site, NiteWhite EXCEL 2 NSF 10%, Standard Kit; DayWhite 2 "Z" 7.5% (Jul. 11, 2002).

Ultradent Products Web Site, Opalescence Xtra, Sep. 16, 1997 (or.Aug. 2002); Opalescence Xtra Boost (Apr. 30, 2002).

Frysh et al., "Effect of pH on Hydrogen Peroxide Bleaching Agents," *Journal of Aesthetic Dentistry*, vol. 7, No. 3 (1995), pp. 130-133.

* cited by examiner

*Primary Examiner*—Frederick Krass
(74) *Attorney, Agent, or Firm*—Christie, Parker & Hale, LLP

(57) ABSTRACT

A two-component tooth whitening system which incorporates an increased peroxide content, wherein the components are adapted to be mixed and applied to the teeth from a dental bleaching tray is provided. A first component includes both carbamide peroxide and hydrogen peroxide and a second component comprises an orally compatible activator gel.

24 Claims, No Drawings

INCREASED PEROXIDE CONTENT TOOTH BLEACHING GEL

CROSS-REFERENCE TO RELATED APPLICATIONS

This application is a continuation of patent application Ser. No. 10/349,725, filed Jan. 22, 2003 now abandoned, which is a continuation of patent application Ser. No. 09/659,483, filed Sep. 11, 2000 now abandoned, which claims the benefit of the filing date of provisional patent application Ser. No. 60/153,162, filed on Sep. 9, 1999; the entire contents of the foregoing applications are expressly incorporated herein by reference.

FIELD OF THE INVENTION

This invention relates to tooth whitening compositions and, more particularly, to a two-component tooth whitening system which incorporates an increased peroxide content, wherein the components are adapted to be admixed and applied to the teeth from a dental bleaching tray.

BACKGROUND OF THE INVENTION

In that aspect of aesthetic dentistry which relates to self-administered use of in-home tooth whitening compositions, the dental patient is provided with a custom-fitted dental try adapted to receive a whitening gel that is dispensed from a syringe. The dental tray, with its gel content, is unobtrusively and advantageously worn by the patient during the day or at night and while the patient sleeps. This treatment is repeated for a sufficient period of time to effect the tooth bleaching and whitening process.

It is disclosed in the prior art that hydrogen peroxide, carbamide peroxide (urea peroxide) and other peroxides can be used as the whitening agents in the formulation of tooth whitening gels. The prior art also discloses that carboxypolymethylene (Carbopol), poloxamer (Pluronic), and cellulosic gums, as well as other thickeners, can be used as the gelling agent in the preparation of peroxide gels. The gels can be water based or anhydrous.

U.S. Pat. No. 4,528,180 (Schaeffer, 1985), U.S. Pat. No. 4,687,663 (Schaeffer, 1987) and U.S. Pat. No. 4,849,213 (Schaeffer, 1989) disclose a two-component dental product wherein a first component comprises a dental gel containing, for example, hydrogen peroxide, water, Carbopol 934, Pluronic F127, hydroxypropyl methyl cellulose and sodium hydroxide, and the second component comprises an aqueous dental paste containing, for example, sodium bicarbonate, sodium chloride, glycerin, propylene glycol, thickener and polishing agent. The first and second components are adapted to be simultaneously dispensed onto a toothbrush for application to the teeth. The patentee points out that the two-component system provides the oral care benefits achieved through the combination of hydrogen peroxide, sodium bicarbonate and table salt and overcomes the hydrogen peroxide dissociation that would arise through the unitary packaging of these ingredients, since hydrogen peroxide and sodium bicarbonate immediately react upon mixing.

A prior art product produced by applicant and sold under the DAY WHITE trademark is provided in a double-barrel syringe with approximately equal amounts of a peroxide gel formulation in one barrel and a booster gel in the other.

The peroxide gel formulation consists of the following:

| Peroxide Gel | | |
|---|---|---|
| Deionized water | — | 13.050% |
| Propylene glycol | USP | 14.000% |
| Glycerine | USP | 11.000% |
| Xylitol | FG | 5.00% |
| Hydrogen peroxide (50%) | CG | 30.000% |
| Poloxamer 407 | USP/NF | 26.000% |
| Flavor | FG | 0.700% |
| Eugenol | USP | 0.250% |
| Antifoaming agent | USP/NF | q.s. |

The booster gel formulation consists of the following:

| Booster Gel | | |
|---|---|---|
| Deionized water | — | 53.400% |
| Glycerine | USP | 19.500% |
| Propylene glycol | USP | 5.000% |
| Poloxamer 407 | USP/NF | 20.000% |
| Flavor | FG | 0.700% |
| Color | FG | 0.400% |
| Potassium hydroxide | USP | 0.500% |
| Aloe vera | | 0.500% |
| Antifoaming agent | USP/NF | q.s. |

When the DAY WHITE product is dispensed from the double-barrel syringe, the peroxide gel formulation mixes together with the booster gel formulation and in the mixed condition is dispensed into a flexible tray which is placed by the patient on his teeth.

There is a need in the art for a two-component tooth whitening composition with increased peroxide content to facilitate the tooth whitening process.

SUMMARY OF THE INVENTION

There is therefore provided in accordance with practice of one embodiment of the present invention a tooth bleaching gel composition comprising carbamide peroxide and hydrogen peroxide in the absence of a radiant-energy or heat-energy absorbing activator substance. In another embodiment of the present invention, a two-component dental bleaching system is provided, wherein the components are adapted to be admixed and applied to the teeth from a dental tray for sustained contact. The system comprises as a first component a dental peroxide gel comprising both carbamide peroxide and aqueous hydrogen peroxide and as a second component an orally compatible activator gel.

DETAILED DESCRIPTION OF THE INVENTION

The dental bleaching compositions of this invention comprise a two-component system. As a first component there is provided an orally compatible peroxide bleaching gel. Various peroxide and peroxy compositions can be used in the preparation of the bleaching gels. However, carbamide peroxide (Merck Index #10007, 12th Ed.) and hydrogen peroxide are particularly well suited and are preferred as the bleaching agents. The carbamide peroxide is generally present in the bleaching gel in an amount from about 10% by weight to about 25% by weight, and, preferably, in an amount from about 12% to about 18% by weight. The hydrogen peroxide is preferably provided as a 50% aqueous solution and is generally present in an amount of from about 1% to about 20% (0.5% to 10% in the absence of water); preferably in an amount of from about 5% to about 14% (5% to 17% in the absence of water).

In one embodiment of the present invention, the bleaching gel has a pH from about 5 to about 8. Preferably, the pH is from about 5.5 to about 6.5.

Gelling agents which can be used in the preparation of bleaching gels include, for example, cellulosic gums, fumed silica, for example, CAB-O-SIL fumed silica provided by Cabot Corporation, and emulsifying waxes such as Polawax or Crodafos CES formulations provided by Croda, Inc., and mixtures thereof in amounts to provide a high strength dental peroxide gel. The presently preferred cellulosic gum is Klucel® GFF which is a trademark for hydroxypropyl cellulose (Merck Index #4888, 12th Ed.).

Adjuvants and minor use ingredients are advantageously included in the formulation to improve gel consistency and provide flavor and taste enhancements. To improve gel consistency, the dental bleaching composition can be formulated with gel modifying aliphatic polyols in an amount from about 5% to about 30% by weight. Preferred polyols include glycerine (Merck Index #4493, 12th Ed.) in an amount of from about 2% to about 25% by weight and propylene glycol (Merck Index #8040, 12th Ed.) in amount of from about 14% to about 55% by weight.

In one exemplary embodiment of preparation of the bleaching gels of the present invention, the ingredients of the bleaching gel are mixed together in a mixer provided by Scott Turbon Mixer, Inc., of Adelanto, Calif., identified as Model No. KBV 50.20 (Serial No. 3924.1). The mixer has two blade systems, one being a relatively low speed paddle system (hereinafter called "scrape"), and the other being a high speed mixer system (hereinafter called "turbon"). The scrape and turbon systems can be adjusted to different speeds identified as Hertz (Hz) settings. For example, a setting of 30 Hz represents a given speed with higher hertz settings being higher speeds and lower Hz settings being lower speeds.

In a first step of preparing the bleaching gel, a propylene glycol component and a Klucel GFF component are added to the mixer and mixed together with both blade systems in operation (scrape at 30 Hz, turbon at 35 Hz) under a vacuum of 28 in. Hg for about 45–90 minutes or until the Klucel GFF is completely dispersed. Mixing is done at room temperature, and a water jacket is provided on the outside surface of the mixer to remove heat which is generated by the mixing process. Glycerine is added and then mixed using only the scrape system at 15 Hz under the 28 in. Hg vacuum until it is dispersed. When a second listed propylene glycol component is present, it is added and mixed into the formulation after the glycerine addition. The vacuum is then turned off and CAB-O-SIL EH-5 is then added and mixed after restoring the vacuum to 28 in. Hg using only the scrape system at 30 Hz until the CAB-O-SIL is completely dispersed. In another embodiment both the scrape and turbon systems are used with both set at 15 Hz. In this embodiment after the CAB-O-SIL has been dispersed the turbon is turned off, the blades cleaned, the vacuum restored and mixing with the scrape system is continued for 30 minutes. Carbamide peroxide is then added and mixed for about 30–80 minutes or until it is completely dissolved using the scrape system at 30 Hz under the 28 in. Hg vacuum. In another embodiment, the carbamide peroxide is added and mixed for about 30–80 minutes or until it is completely dissolved using the turbon system at 15 Hz and the scrape system at 20 Hz under 28 in. Hg vacuum. It is noted that after the addition of carbamide peroxide the temperature in the batch is controlled not to exceed 95° F. Polawax and glycerine are mixed in a suitable stainless steel container, melted together by heating at 50–60° C., and then allowed to cool until reaching about 40° C. The melted wax/glycerine mixture is then added to the batch with the turbon system off. Subsequently, aqueous hydrogen peroxide (50% by weight water) is added and mixed for about 10–15 minutes under very low speed mixing condition, scrape 10 Hz, turbon 15 Hz under continued vacuum at 28 in. Hg. After addition of the wax mixture and hydrogen peroxide, the batch temperature must be controlled not to exceed 120° F.

Non-limiting examples of whitening gels provided in accordance with practice of the present invention are as follows:

| Ingredients | Formula Amount | Unit | % Wt/Wt |
|---|---|---|---|
| Bleaching Gel 1 | | | |
| Propylene Glycol USP | 89.1 | lb | 33.000% |
| Klucel GFF | 2427.1 | gm | 1.980% |
| Glycerine USP | 25.5 | lb | 9.420% |
| CAB-O-SIL EH-5 | 12.2 | lb | 4.500% |
| Carbamide Peroxide USP | 43.7 | lb | 16.200% |
| Hydrogen Peroxide 50% CG | 31.9 | lb | 11.800% |
| Glycerine USP | 38.0 | lb | 14.000% |
| Polawax NF | 24.3 | lb | 9.000% |
| Total | 270.0 | | 100.000% |
| Bleaching Gel 2 | | | |
| Propylene Glycol USP | 99.0 | lb | 33.000% |
| Klucel GFF | 5.9 | lb | 1.980% |
| Glycerine USP | 35.8 | lb | 11.920% |
| CAB-O-SIL EH-5 | 13.5 | lb | 4.500% |
| Carbamide Peroxide USP | 48.6 | lb | 16.200% |
| Polawax NF | 19.5 | lb | 6.500% |
| Glycerine USP | 42.3 | lb | 14.100% |
| Hydrogen Peroxide 50% CG | 35.4 | lb | 11.800% |
| Antifoaming agent | q.s. | | q.s. |
| Total | 300.0 | | 100.000% |
| Bleaching Gel 3 | | | |
| Propylene Glycol USP | 99.0 | lb | 33.000% |
| Klucel GFF | 5.9 | lb | 1.980% |
| Glycerine USP | 25.3 | lb | 8.420% |
| Propylene Glycol USP | 26.7 | lb | 8.900% |
| CAB-O-SIL EH-5 | 13.5 | lb | 4.500% |
| Carbamide Peroxide USP | 48.6 | lb | 16.200% |
| Polawax NF | 24.0 | lb | 8.000% |
| Glycerine USP | 48.3 | lb | 16.100 |
| Hydrogen Peroxide 50% CG | 8.7 | lb | 2.900% |
| Antifoaming agent | q.s. | | q.s. |
| Total | 300.0 | | 100.000% |
| Bleaching Gel 4 | | | |
| Propylene Glycol USP | 99.0 | lb | 33.000% |
| Klucel GFF | 5.9 | lb | 1.980% |
| CAB-O-SIL EH-5 | 13.5 | lb | 4.500% |
| Carbamide Peroxide USP | 48.6 | lb | 16.200% |
| Polawax NF | 19.5 | lb | 6.500% |
| Glycerine USP | 52.9 | lb | 17.620% |
| Hydrogen Peroxide 50% CG | 60.6 | lb | 20.200% |
| Antifoaming agent | q.s. | | q.s. |
| Total | 300.0 | | 100.00% |
| Bleaching Gel 5 | | | |
| Propylene Glycol USP | | | 19.600% |
| Klucel GFF | | | 1.980% |
| Glycerine USP | | | 16.920% |
| CAB-O-SIL EH-5 | | | 4.500% |
| Carbamide Peroxide USP | | | 16.200% |

-continued

| Ingredients | Formula Amount | Unit | % Wt/Wt |
|---|---|---|---|
| Polawax NF | | | 6.500% |
| Glycerine USP | | | 14.100% |
| Hydrogen Peroxide 50% CG | | | 20.200% |
| Antifoaming agent | | | q.s. |
| | | | 100.000% |

As a second component of the two-component system, there is provided an activator gel. Gelling agents which can be used in the preparation of the activator gels include cellulosic gums such as Klucel GFF, fumed silica, and mixtures thereof. In one embodiment of the present invention, the activator gel has a pH of from about 9 to about 10; preferably, about 9.5.

To improve the activator gel consistency and to provide flavor and color enhancements, adjuvants and minor use ingredients are advantageously incorporated into the activator gel formation. With respect to improving activator gel, consistency, the activator gel can be formulated with gel modifying aliphatic polyols in an amount of from about 40% to 85% by weight. Preferred polyols include glycerine in an amount of from about 5% to about 45% by weight and propylene glycol in an amount of from about 20% to 60% by weight.

The activator gels can include a desensitizer in order to reduce tissue sensitivity and encourage compliance with the bleaching procedure. A preferred desensitizer is potassium nitrate from about 4% to about 10% by weight. A flavoring agent such as peppermint flavor can be present in the formulation in an amount up to about 0.5% by weight. In some embodiments of the activator gels provided in accordance with the present invention, sodium fluoride is added to protect the teeth against caries.

Non-limiting examples of activator gels provided in accordance with one embodiment of practice of the present invention are as follows:

| Ingredients | Formula Amount | Unit | % Wt/Wt |
|---|---|---|---|
| Activator Gel 1 | | | |
| Propylene Glycol USP | 95.7 | lb | 33.000% |
| Klucel GFF | 2606.9 | gm | 1.980% |
| Aloe Vera, pwd (Activera 1200-A) | 329.2 | gm | 0.250% |
| Sodium Fluoride USP | 460.8 | gm | 0.350% |
| Propylene Glycol USP | 27.3 | lb | 9.420% |
| Glycerine USP | 116.0 | lb | 40.000% |
| Peppermint PE-07274 | 263.3 | gm | 0.200% |
| Natural Peppermint Oil PE-05523 | 526.6 | gm | 0.400% |
| CAB-O-SIL EH-5 | 21.5 | lb | 7.400% |
| Potassium Nitrate FCC | 20.3 | lb | 7.000% |
| Total | 290.0 | | 100.000% |
| Activator Gl 2 | | | |
| Propylene Glycol USP | 79.2 | lb | 33.000% |
| Klucel GFF | 2157.4 | gm | 1.980% |
| Aloe Vera, pwd (Activera 1200-A) | 272.4 | gm | 0.250% |
| Propylene Glycol USP | 24.4 | lb | 10.170% |
| Glycerine USP | 96.0 | lb | 40.000% |
| Peppermint PE-07274 | 217.9 | gm | 0.200% |

-continued

| Ingredients | Formula Amount | Unit | % Wt/Wt |
|---|---|---|---|
| Natural Peppermint Oil PE-05523 | 435.8 | gm | 0.400% |
| CAB-O-SIL EH-5 | 16.8 | lb | 7.000% |
| Potassium Nitrate FCC | 16.8 | lb | 7.000% |
| Total | 240.0 | | 100.000% |
| Activator Gel 3 | | | |
| Propylene Glycol USP | 95.7 | lb | 33.000% |
| Klucel GFF | 2606.9 | gm | 1.980% |
| Aloe Vera, pwd (Activera 1200-A) | 329.2 | gm | 0.250% |
| Sodium Fluoride USP | 460.8 | gm | 0.350% |
| Propylene Glycol USP | 47.3 | lb | 16.320% |
| Glycerine USP | 116.0 | lb | 40.000% |
| Peppermint PE-07274 | 263.3 | gm | 0.200% |
| Natural Peppermint Oil PE-05523 | 526.6 | gm | 0.400% |
| CAB-O-SIL EH-5 | 21.8 | lb | 7.500% |
| Total | 290.0 | | 100.000% |
| Activator Gel 4 | | | |
| Propylene Glycol USP | 95.7 | lb | 33.000% |
| Klucel GFF | 2606.9 | gm | 1.980% |
| Aloe Vera, pwd (Activera 1200-A) | 329.2 | gm | 0.250% |
| Propylene Glycol USP | 49.8 | lb | 17.170% |
| Glycerine USP | 116.0 | lb | 40.000% |
| Peppermint PE-07274 | 263.3 | gm | 0.200% |
| Natural Peppermint Oil PE-05523 | 526.6 | gm | 0.400% |
| CAB-O-SIL EH-5 | 20.3 | lb | 7.000% |
| Total | 290.0 | | 100.000% |
| Activator Gel 5 | | | |
| Propylene Glycol USP | 99.0 | lb | 33.000% |
| Klucel GFF | 2696.8 | gm | 1.980% |
| Aloe Vera, pwd (Activera 1200-A) | 340.5 | gm | 0.250% |
| Propylene Glycol USP | 49.8 | lb | 16.592% |
| Glycerine USP | 120.0 | lb | 40.000% |
| Peppermint PE-07274 | 272.4 | gm | 0.200% |
| Natural Peppermint Oil PE-05523 | 544.8 | gm | 0.400% |
| CAB-O-SIL EH-5 | 21.3 | lb | 7.100% |
| Tetrapotassium Pyrophosphate | 250.6 | gm | 0.184% |
| DI Water | 400.4 | gm | 0.294% |
| Total | 300.0 | | 100.000% |
| Activator Gel 6 | | | |
| Propylene Glycol USP | 141.9 | lb | 33.000% |
| Klucel GFF | 3865.4 | gm | 1.980% |
| Aloe Vera, pwd (Activera 1200-A) | 488.1 | gm | 0.250% |
| Sodium Fluoride USP | 683.3 | gm | 0.350% |
| Propylene Glycol USP | 40.5 | lb | 9.420% |
| Glycerine USP | 172.0 | lb | 40.000% |
| Peppermint PE-07274 | 390.4 | gm | 0.200% |
| Natural Peppermint Oil PE-05523 | 780.9 | gm | 0.400% |
| CAB-O-SIL EH-5 | 31.8 | lb | 7.400% |
| Potassium Nitrate FCC | 30.1 | lb | 7.000% |
| Total | 430.0 | | 100.000% |
| Activator Gel 7 | | | |
| Propylene Glycol USP | 141.9 | lb | 33.000% |
| Klucel GFF | 3865.4 | gm | 1.980% |
| Aloe Vera, pwd (Activera 1200-A) | 488.1 | gm | 0.250% |
| Sodium Fluoride USP | 683.3 | gm | 0.350% |
| Propylene Glycol USP | 67.2 | lb | 15.620% |

-continued

| Ingredients | Formula Amount | Unit | % Wt/Wt |
|---|---|---|---|
| Glycerine USP | 172.0 | lb | 40.000% |
| Peppermint PE-07274 | 390.4 | gm | 0.200% |
| Natural Peppermint Oil PE-05523 | 780.9 | gm | 0.400% |
| CAB-O-SIL EH-5 | 35.3 | lb | 8.200% |
| Total | 430.0 | | 100.000% |

Activator Gel 8

| Ingredients | Formula Amount | Unit | % Wt/Wt |
|---|---|---|---|
| Propylene Glycol USP | 141.9 | lb | 33.000% |
| Klucel GFF | 3865.4 | gm | 1.980% |
| Aloe Vera, pwd (Activera 1200-A) | 488.1 | gm | 0.250% |
| Sodium Fluoride USP | 683.3 | gm | 0.350% |
| Propylene Glycol USP | 67.2 | lb | 15.620% |
| Glycerine USP | 172.0 | lb | 40.000% |
| Art. Cherry CH-05506 | 1171.3 | gm | 0.600% |
| CAB-O-SIL EH-5 | 35.3 | lb | 8.200% |
| Total | 430.0 | | 100.000% |

Activator Gel 9

| Ingredients | Formula Amount | Unit | % Wt/Wt |
|---|---|---|---|
| Propylene Glycol USP | 141.9 | lb | 33.000% |
| Klucel GFF | 3865.4 | gm | 1.980% |
| Aloe Vera, pwd (Activera 1200-A) | 488.1 | gm | 0.250% |
| Sodium Fluoride USP | 683.3 | gm | 0.350% |
| Propylene Glycol USP | 40.5 | lb | 9.420% |
| Glycerine USP | 172.0 | lb | 40.000% |
| Art. Cherry CH-05506 | 1171.3 | gm | 0.600% |
| CAB-O-SIL EH-5 | 31.8 | lb | 7.400% |
| Potassium Nitrate FCC | 30.1 | lb | 7.000% |
| Total | 430.0 | | 100.000% |

Activator Gel 10

| Ingredients | Formula Amount | Unit | % Wt/Wt |
|---|---|---|---|
| Propylene Glycol USP | | | 33.000% |
| Klucel GFF | | | 1.980% |
| Aloe Vera, pwd (Activera 1200-A) | | | 0.250% |
| Propylene Glycol USP | | | 7.767% |
| Glycerine USP | | | 31.000% |
| Peppermint Oil PE-07274 | | | 0.200% |
| Natural Peppermint Oil PE-05523 | | | 0.400% |
| CAB-O-SIL EH-5 | | | 5.600% |
| Potassium Nitrate FCC | | | 5.400% |
| DI Water | | | 12.600% |
| Tetrapotassium Pyrophosphate | | | 1.803% |
| Total | | | 100.000% |

Activator Gel 11

| Ingredients | Formula Amount | Unit | % Wt/Wt |
|---|---|---|---|
| Propylene Glycol USP | | | 33.000% |
| Klucel GFF | | | 1.980% |
| Aloe Vera, pwd (Activera 1200-A) | | | 0.250% |
| Propylene Glycol USP | | | 3.842% |
| Glycerine USP | | | 35.000% |
| Artificial Cherry | | | 0.600% |
| CAB-O-SIL EH-5 | | | 7.100% |
| Potassium Nitrate FCC | | | 5.400% |
| DI Water | | | 12.752% |
| Tetrapotassium Pyrophosphate | | | 0.076% |
| Total | | | 100.000% |

Activator Gel 12

| Ingredients | Formula Amount | Unit | % Wt/Wt |
|---|---|---|---|
| Propylene Glycol USP | | | 33.000% |
| Klucel GFF | | | 1.980% |
| Aloe Vera, pwd (Activera 1200-A) | | | 0.250% |
| Propylene Glycol USP | | | 7.767% |
| Glycerine USP | | | 31.000% |
| Peppermint Oil PE-07274 | | | 0.200% |
| Natural Peppermint | | | 0.400% |
| Oil PE-05523 | | | |
| CAB-O-SIL EH-5 | | | 5.600% |
| Potassium Nitrate FCC | | | 5.400% |
| DI Water | | | 9.533% |
| Tetrapotassium Pyrophosphate | | | 4.870% |
| Total | | | 100.000% |

In one embodiment of the processes for preparing the activator gels which incorporate potassium nitrate (activator gels 1, 2–6, and 9–12), in a first step, the first-listed propylene glycol component and the Klucel GFF component are added to the KBV 50 mixer and are mixed together at a 28 in. Hg vacuum using the scrape system at 30 Hz and the turbon system at 35 Hz for about 30 minutes or until the components are dispersed. In another embodiment, the Klucel GFF and first-listed propylene glycol component are first mixed together until completely dispersed in a premix tank and after mixing are added to the KBV 50 mixer and mixed for at least 5 minutes at a scrape setting of 17 Hz. In a second step, the aloe vera component is added and mixed for a minimum of about 5 minutes using the scrape system at 17 Hz at 28 in. Hg vacuum. In the next step, the sodium fluoride component (activator gels 1–6 and 9) is slowly added and mixed using the same scrape setting for about 30 minutes until the sodium fluoride is completely dissolved. In the next step, the second-listed propylene glycol component is added and mixed at 17 Hz (28 in. Hg vacuum) followed by the addition of the glycerine component which is mixed under a vacuum of 28 in. Hg for at least 5 minutes using the scrape setting at 17 Hz until dispersed. In the next step, Peppermint PE-07274 and Natural Peppermint Oil PE-05523 are added to the batch and mixed using only the scrape system at 17 Hz for about 5 minutes. The vacuum is then turned off and the CAB-O-SIL EH-5 component is added, the vacuum is then restored and mixing continues under the same conditions as the previous steps until the CAB-O-SIL is completely dispersed. Finally, the potassium nitrate component is dissolved in DI water and heated to 50–60° C., tetrapotassium pyrophosphate is then added to the heated DI water and the mixture is added to the batch and mixed for about 15 minutes or until it is dispersed using the scrape setting at about 8 Hz.

A similar process is used for mixing activator gels 3, 4, 5, 7 and 8.

The peroxide gel and activator gels are adapted to be admixed and dispensed into a dental bleaching tray such as a custom fitted dental tray for application to the teeth to be whitened. In a preferred embodiment, the peroxide gel and activator gel are packaged in separate barrels of a double-barrel syringe having a closure cap which is replaced with a static mixer at the time of use. The application of manual force to the syringe actuator at the time of use forces the gels into and through the static mixer where the gels are thoroughly mixed and then dispensed into the dental bleaching tray for application to the teeth to be whitened. The pH of the bleaching gel/activator gel mixture is preferably from about 7.5 to about 9.0. More Preferably, the pH is about 8.0.

In practice of the present invention, any of the peroxide gels described above can be combined in the syringe with any one of the activator gels described above and the mixture applied to the teeth.

The above descriptions of preferred embodiments of bleaching gels and activator gels are for illustrative purposes. Because of variations which will be apparent to those skilled in the art, the present invention is not intended to be limited to the particular embodiments described above. It should be understood that the peroxide gel and activator gel compositions of the present invention can function in accordance with practice of the invention in the absence of any elements or materials not specifically described herein as being part of the composition. For example, neither the bleaching gel nor activator gel incorporates a radiant-energy or heat-energy absorbing substance used as an activator.

Examples of radiant-energy and heat-energy absorbing activator substances are set forth in U.S. Pat. No. 5,858,332 as follows: "Activation of the dental bleaching composition of the present invention is accomplished with a bleaching agent activator that is preferably a radiant-energy or heat-energy absorbing substance. Examples of such substances include radiant-energy absorbing, substantially conjugated hydrocarbons such as aromatic hydrocarbons, multiple double-bond hydrocarbon chains, chain-aromatic mixtures, reacted combinations thereof, and equivalents. Specific examples include caroteneoids such as bixin, lycoxanthin, lycophil, canthaxanthin, capsanthin, cryptoxanthin, isomers of carotene, and lycopene. Other specific examples include aromatics such as coronene, fluoranthene, naphtho [2,3-a] pyrene, trans-4,4'-diphenylstilbene, 9,10-diphenylanthracene, 5,12-bis(phenyethynyl)napthacene, 9,10-bis(phenylethynyl)anthracene, and perylene. The foregoing compounds may optionally include one or more carboxyl groups. The only limitations are (1) that the radiant-energy absorbing substance does not cause substantial peroxide decomposition over time, and (2) that the radiant-energy absorbing substance be substantially peroxide resistant in the presence of the bleaching agent over time. Preferred bleaching agent activators include 9,10-bis(phenylethynyl) anthracene, perylene, and isomers of carotene and carboxyl-substituted variations thereof." (Col. 4, lines 1–24). U.S. Pat. No. 5,858,332 is incorporated herein by reference.

The invention claimed is:

1. A two-component dental bleaching system wherein the components are adapted to be admixed and applied to teeth from a dental tray for sustained contact, said system comprising:
    as a first component, a dental peroxide gel comprising both carbamide peroxide and hydrogen peroxide; and
    as a second component, an orally compatible activator gel wherein said 2-component bleaching system is activatable without application of heat or radiant energy.

2. The dental bleaching system according to claim 1, wherein the first component includes hydroxypropyl cellulose.

3. The dental bleaching system according to claim 1, wherein the first component comprises carbamide peroxide at a weight percentage of at least about 10%, based on the total weight of said first component.

4. The dental bleaching system according to claim 1, wherein the first component comprises hydrogen peroxide at a weight percentage of at least about 0.5%. based on the total weight of the first component.

5. The dental bleaching system according to claim 1, wherein the first component comprises hydrogen peroxide at a weight percentage of at least about 5%, based on the total weight of the first component.

6. The dental bleaching system according to claim 1, wherein the first component comprises carbamide peroxide at a weight percentage of at least about 16% and hydrogen peroxide at a weight percentage of at least about 1.5%, based on the total weight of the first component.

7. The dental bleaching system according to claim 1, wherein the first component comprises carbamide peroxide at a weight percentage from about 10% to about 25% and hydrogen peroxide at a weight percentage from about 0.5% to about 10%, based on the total weight of the first component.

8. The dental bleaching system according to claim 1, wherein the first component comprises carbamide peroxide at about 16% by weight and hydrogen peroxide at about 1.3% by weight, based on the total weight of the first component.

9. The dental bleaching system according to claim 1, wherein the first component comprises carbamide peroxide at about 16% by weight and hydrogen peroxide at about 6% by weight, based on the total weight of the composition.

10. The dental bleaching system according to claim 1, wherein the first component comprises carbamide peroxide at a weight percentage of about 16% and hydrogen peroxide at a weight percentage of about 10%. based on the total weight of the composition.

11. The dental bleaching system according to claim 1, wherein the activator gel comprises sodium fluoride and potassium nitrate.

12. The dental bleaching system according to claim 1, wherein the activator gel comprises potassium nitrate and tetrapotassium pyrophosphate.

13. A two-component dental bleaching system, wherein the components are adapted to be admixed and applied to teeth from a dental tray for sustained contact, said system comprising:
    as a first component, a dental peroxide gel comprising:

| | |
|---|---|
| Propylene Glycol | 41.9% by wt. |
| Hydroxypropyl Cellulose | 1.98% by wt. |
| Glycerine | 24.52% by wt. |
| Fumed Silica | 4.5% by wt. |
| Carbamide Peroxide | 16.2% by wt. |
| Emulsifying Wax | 8.0% by wt. |
| Hydrogen Peroxide 50% | 2.9% there and |
| Antifoaming Agent | q.s. |

14. A two-component dental bleaching system, wherein the components are adapted to be admixed and applied to teeth from a dental tray for sustained contact, said system comprising:
    as a first component, a dental peroxide gel comprising:

| | |
|---|---|
| Propylene Glycol | 33.0% by wt. |
| Hydroxypropyl Cellulose | 1.980%; by wt. |
| Glycerin | 26.02% by wt. |
| Fumed Silica | 26.02% by wt. |
| Carbamide Peroxide | 16.2% by wt. |
| Emulsifying Wax | 6.5% by wt. |
| Hydrogen Peroxide 50% | 11.8% by wt. and |
| Antifoaming Agent | q.s. |

15. A two-component dental bleaching system, wherein the components are adapted to be admixed and applied to teeth from a dental tray for sustained contact, said system comprising:
    as a first component, a dental peroxide gel comprising:

| | |
|---|---|
| Propylene Glycol USP | 33.0% by wt. |
| Hydroxypropyl Cellulose | 1.98% by wt. |
| Glycerine | 31.02% by wt. |
| Fumed Silica | 4.5% by wt. |
| Carbamide Peroxide | 16.2% by wt. |
| Emulsifying Wax | 6.5% by wt. |
| Hydrogen Peroxide 50% | 20.2% there by wt. |
| Antifoaming Agent | q.s. |

16. A two component tooth bleaching system comprising a dual barrel syringe wherein the first barrel contains a bleaching gel composition comprising carbamide peroxide and aqueous hydrogen peroxide and the second barrel contains an orally compatable activator gel, and neither the first nor second component incorporates a radiant energy or heat energy absorbing activator.

17. The two component tooth bleaching system according to claim 16, wherein the bleaching gel composition comprises carbamide peroxide at a weight percentage of at least about 10%, based on the total weight of the composition.

18. The two component tooth bleaching system according to claim 16, wherein the bleaching gel composition comprises hydrogen peroxide at a weight percentage of at least about 0.5%, based on the total weight of the composition.

19. The two component tooth bleaching system according to claim 16, wherein the composition comprises hydrogen peroxide at a weight percentage of at least about 5%, based on the total weight of the composition.

20. The two component tooth bleaching system according to claim 16, wherein the composition comprises carbamide peroxide at a weight percentage of at least about 16% and hydrogen peroxide at a weight percentage of at least about 1.5%, based on the total weight of the composition.

21. The two component tooth bleaching system according to claim 16, wherein the composition comprises carbamide peroxide at a weight percentage from about 10% to about 25% and hydrogen peroxide at a weight percentage from about 0.5% to about 10%, based on the total weight of the composition.

22. The two component tooth bleaching system according to claim 16, wherein the composition comprises carbamide peroxide at about 16% by weight and hydrogen peroxide at about 1.3% by weight, based on the total weight of the composition.

23. The two component tooth bleaching system according to claim 16, wherein the composition comprises carbamide peroxide at about 16% by weight and hydrogen peroxide at about 6% by weight, based on the total weight of the composition.

24. The two component tooth bleaching system gel composition according to claim 16, wherein the composition comprises carbamide peroxide at a weight percentage of about 16% and hydrogen peroxide at a weight percentage of about 10%, based on the total weight of the composition.

* * * * *

UNITED STATES PATENT AND TRADEMARK OFFICE
CERTIFICATE OF CORRECTION

PATENT NO. : 7,060,256 B2  Page 1 of 1
APPLICATION NO. : 10/758915
DATED : June 13, 2006
INVENTOR(S) : Pellico It is certified that error appears in the above-identified patent and that said Letters Patent is hereby corrected as shown below:

Column 9, line 59,    Delete "0.5%.",
                      Insert --0.5%,--

Column 10, line 21,   Delete "10%.",
                      Insert --10%,--

Column 10, line 43,   Delete "there and",
                      Insert --by wt. and--

Column 11, line 4,    Delete "USP"

Column 11, line 10,   Delete "there by wt.",
                      Insert --by wt. and--

Signed and Sealed this

Third Day of October, 2006

JON W. DUDAS
*Director of the United States Patent and Trademark Office*